United States Patent [19]

Meyer et al.

[11] 3,933,893

[45] Jan. 20, 1976

[54] DERIVATIVES OF 9-PHENANTHRENE

[75] Inventors: Donald R. Meyer; Arthur D. Sill, both of Cincinnati, Ohio

[73] Assignee: Richardson-Merrell Inc., Wilton, Conn.

[22] Filed: Sept. 13, 1974

[21] Appl. No.: 505,661

Related U.S. Application Data

[62] Division of Ser. No. 317,146, Dec. 21, 1972, Pat. No. 3,859,312.

[52] U.S. Cl.... 260/468.5; 260/247.2 B; 260/293.56; 260/293.58; 260/293.59; 260/295 T; 260/326.34; 260/326.43; 260/343.2; 260/473 F; 260/475 R; 260/475 F; 424/248; 424/263; 424/267; 424/274; 424/279; 424/283

[51] Int. Cl.².......................................... C07C 93/20

[58] Field of Search..... 260/468.5, 247.2 B, 293.56, 260/326.43

[56] References Cited

OTHER PUBLICATIONS

Feisen, Reagants for Organic Synthesis, pp. 193–194, (1967).

*Primary Examiner*—Robert Gerstl
*Attorney, Agent, or Firm*—William J. Stein; Eugene O. Retter; George W. Rauchfuss, Jr.

[57] ABSTRACT

Novel bis basic esters of 9-substituted phenanthrene and related 9-oxa and 9-aza derivatives thereof, their preparation and use for the prevention and inhibition of viral infections are disclosed.

4 Claims, No Drawings

DERIVATIVES OF 9-PHENANTHRENE

This is a division of application Ser. No. 317,146, filed Dec. 21, 1972, now issued as U.S. Pat. No. 3,859,312.

FIELD OF THE INVENTION

This invention relates to new organic chemical compounds, to their preparation and to pharmaceutical compositions containing these compounds. The compounds described herein are antiviral agents which are useful in inactivating or inhibiting viruses by their administration to either an infected host or to a non-infected host.

BACKGROUND OF THE INVENTION

There is a growing body of information that viruses play a vital role in a broad range of diseases, some of which represent the most serious of man's ills. Arthritis, juvenile arthritis, diabetes, Hodgkin's disease and various immunological diseases and degenerative diseases of the central nervous system have been linked to viruses as the causative agents.

At present, the control of virus infections is primarily achieved by means of immunization vaccines. For example, poliomyelitis, smallpox, measles and influenza are well recognized diseases in which viral vaccines have proven effective. In general, however, viral vaccines have had only a moderate success in animal prophylaxis. Each vaccine acts primarily against a specific virus and is not heterophilic in the protection it offers. Hence, vaccines do not provide a practical solution against the wide array of infectious viruses, even when limited as for example, solely to respiratory viruses.

One approach to the control of virus-related diseases and, particularly to the spread of such virus diseases, has been to search for medicinal agents or chemotherapeutic agents which are capable of inhibiting the growth of viruses, thereby preventing the spread of disease as well as preventing further damage to cells and tissues of the animal host which have not as yet been infected. Heretofore, only a limited number of virus infections such as smallpox, Asian influenza and herpes keratitis have been susceptible to prevention by chemical antiviral agents. Sulfonamides and antibiotics which have revolutionized the treatment of bacterial infections have substantially no effect upon virus infections. Certain infections caused by large viruses, such as lymphogranuloma venereum, psittacosis and trachoma have been successfully treated using antibiotics and sulfa drugs. However, the majority of infections have not been responsive to attack by chemotherapeutic agents. Thus, it can be seen that there is a need for new chemotherapeutic agents which are effective against a broad range of virus diseases, and which at the same time, are non-toxic to the host.

As a result of a long series of investigations, applicants have discovered a novel class of bis-basic esters of phenanthrene and 9-oxa and 9-aza phenanthrene which are particularly useful antiviral agents. These compounds are effective against a wide spectrum of virus infections and are useful in treating such infections either prophylactically or therapeutically.

U.S. Pat. Nos. 3,531,489; 3,647,860 and 3,662,062 represent the closest art known to applicants and disclose esters and thioesters of fluorene, fluorenol, fluorenone and fluoranthene which are useful as antiviral agents. Certain of the compounds disclosed in U.S. Pat. No. 3,662,062 serve as starting materials for the preparation of the compounds of the present invention. The bis-basic esters described and claimed herein, however, are derived from totally different and non-related 6,6,6 membered aromatic ring systems which differ substantially from either the fluorene or fluoranthene nucleus. To applicants' knowledge the compounds described and claimed herein are novel compounds which have not previously been described nor reported in the literature. Furthermore, applicants are unaware of any previously reported bis basic derivatives of phenanthrene or derivatives of 9-oxa and 9-aza phenanthrene whatsoever which possess antiviral activity. The instant compounds possess a wide spectrum of antiviral activity in varying degrees which could not, therefore, have been predicted from a knowledge of the present state of the art.

SUMMARY OF THE INVENTION

This invention relates to new derivatives of 9-substituted phenanthrene and to their related 9-oxa and 9-aza congeners. This invention also relates to methods for their preparation and to their use as pharmaceutical agents. More particularly, the compounds of the present invention are 2,7-bis-basic esters of 9-phenanthrene, or 9-alkoxyphenanthrene, 3,8-bis-basic esters of 6(5H)-phenanthridinone and 3,8-bis-basic esters of 6H-dibenzo[b,d]pyran-6-one which are useful in the prevention or inhibition of virus infections. Still more particularly, the compounds of the present invention may be represented by the following general formulas:

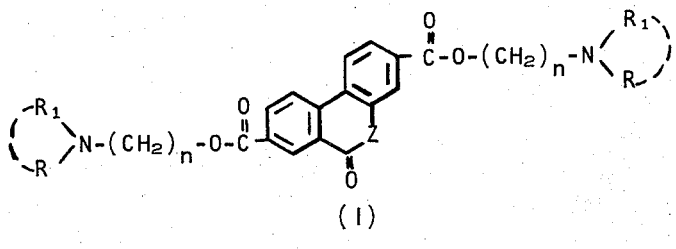

(I)

and

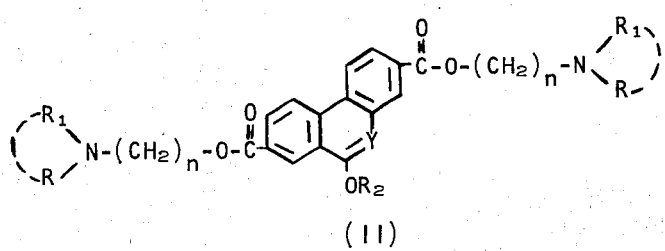

(II)

wherein n is an integer of from 2 to 6; R and $R_1$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than in the 1-position of the alkenyl group, and when R and $R_1$ are taken together with the nitrogen atom to which they are attached represent the pyrrolidinyl, piperidino or morpholino radical; Z is selected from the group consisting of oxygen, nitrogen and methylene; Y is nitrogen or methylidene; and $R_2$ is selected from the group consisting of hydrogen or lower alkyl having from 1 to 4 carbon atoms. The expression methylene is intended to refer to the -CH$_2$- radical, whereas the expression methylidene is intended to refer to the —CH = radical.

The compounds represented in formulas (I) and (II) above include both the free base form as well as the pharmaceutically acceptable acid addition salts thereof. In general, the salts of these compounds are crystalline materials which are soluble in water and various hydrophilic organic solvents, and which, in comparison to their free base forms, demonstrate higher melting points and an increased stability.

It should be noted that the bis-basic ester side chains appear in the same relative configuration for the 9-substituted phenanthrene, 6(5H)-phenanthridinone and the 6H-dibenzo[b,d]pyran-6-one series of compounds. However, due to the difference in numbering systems as shown below, the compounds of the present invention are designated as 2,7-bis-basic esters for the phenanthrene series of compounds, whereas they are designated as 3,8-bis-basic esters in both the phenanthridine and 6H-benzo[b,d]pyran series of compounds.

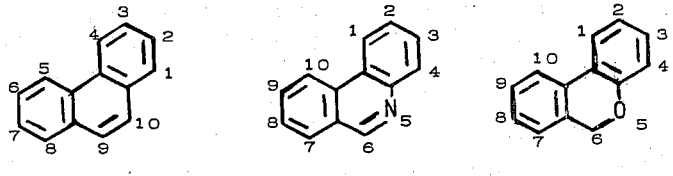

The 2,7-bis basic esters of 9-methoxyphenanthrone (V) are prepared via a ring enlargement of the related 2,7-bis basic esters of fluoren-9-one (III), which are found described in U.S. Pat. No. 3,662,062. This series of reactions can best be illustrated by means of the following reaction scheme in which the symbols n, R, $R_1$ and $R_2$ have the values previously assigned.

The 3,8-bis basic esters of 6(5H)-phenanthridinone

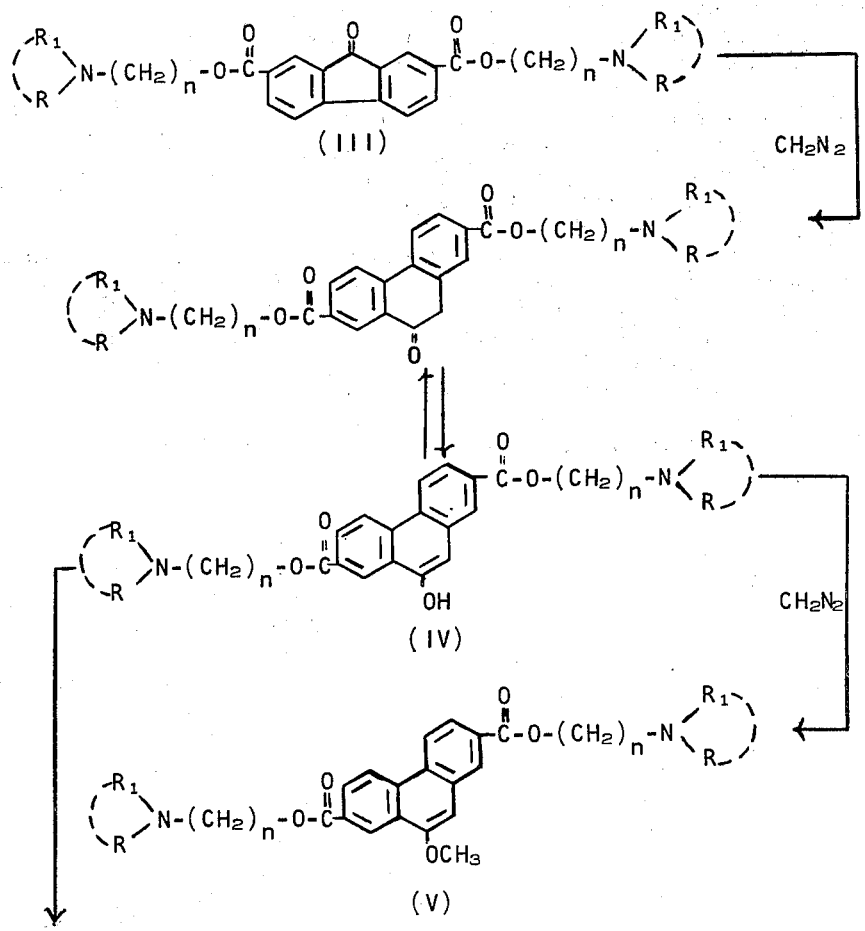

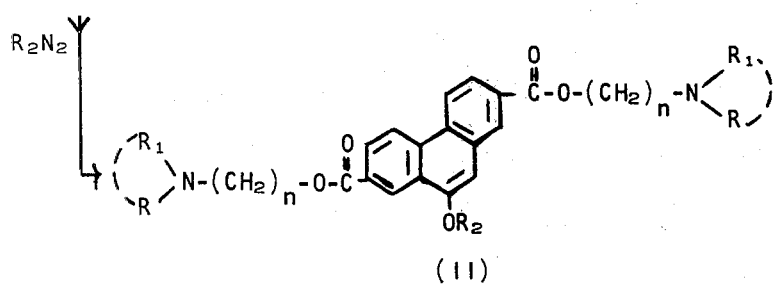

(II)

(VI) are prepared via a hydrazoic acid ring expansion using the same bis basic esters of fluoren-9-one (III) in the presence of a strong mineral acid. This reaction, in which the symbols $n$, R and $R_1$ have the values previously assigned, can be illustrated as follows:

oxidation of fluoren-9-one-2,7-dicarboxylic acid (VII) to form the corresponding 6H-dibenzo[b,d]pyran-6-one-3,8-dicarboxylic acid (VIII). The latter dicarboxylic acid can be esterified with an aminoalkyl halide to form the 6H-dibenzo[b,d]pyran-6-one esters of the

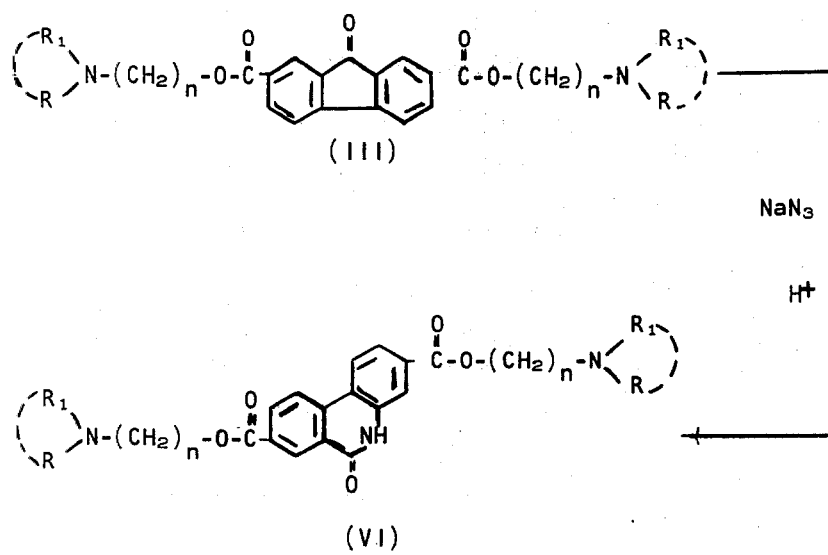

The 3,8-bis-basic esters of 6H-dibenzo[b,d]pyran-6-one (IX) can be prepared by means of a peroxide oxidation present invention, as illustrated by the following general reaction scheme:

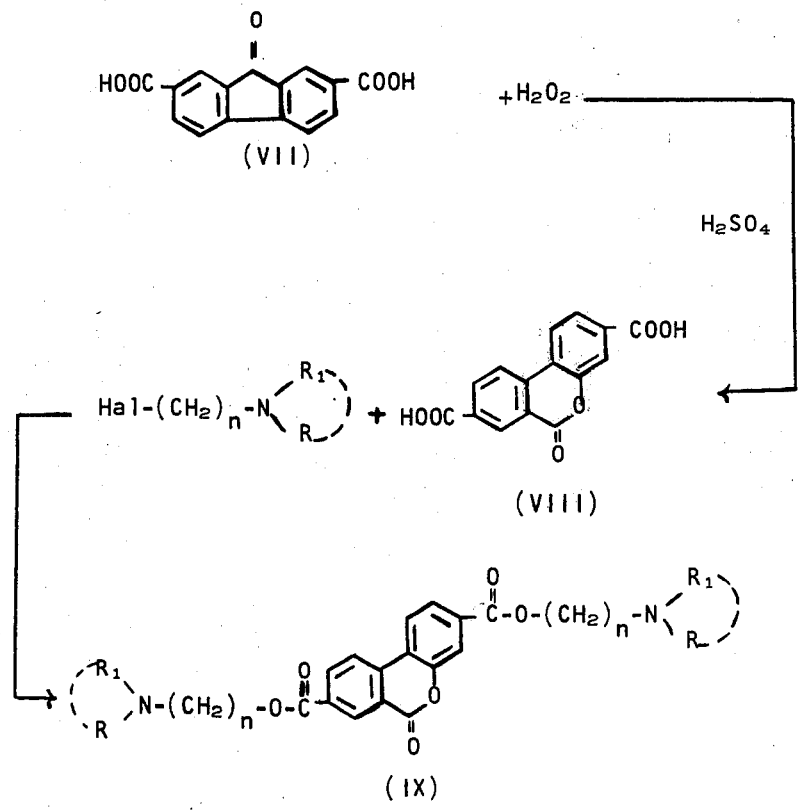

In the above reaction scheme, Hal is chlorine or bromine and n, R and $R_1$ have the values previously assigned.

To achieve an antiviral effect the compounds of this invention are administered to a suitable host using a variety of compositions. Such compositions may be administered either prior to infection, as a prophylactic use or treatment, or they may be therapeutically administered subsequent to infection of the host as a curative use or treatment.

A wide variety of compositions are also included within the scope of the present invention. Thus, the instant compounds may be applied externally or topically directly to the situs of infection, or they may be administered internally or systemically, irrespective of whether the treatment is prophylactic or curative in nature. In either event, replication of the virus is inhibited or prevented with the concomitant result that the various disease symptoms characteristic of the pathogenic virus infection are no longer present.

DETAILED DESCRIPTION OF THE INVENTION

As can be seen from general formulas (I) and (II) above, the compounds of the present invention encompass bis-basic esters in which each side chain is linked to a benzenoid portion of the tricyclic nucleus. Additionally, these side chains are linked at the 2 and 7 positions in the phenanthrene series and at the corresponding 3 and 8 positions in the phenanthridine and 6H-dibenzo[b,d]pyran series. It can be further seen that the side chains consist essentially of a basic amino function at the terminal end of the chain and an ester bridging group at the proximal end of the chain, separated by an alkylene chain of prescribed length.

The basic amino function represented by the symbol

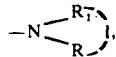

can be a primary, secondary or a tertiary amino group. Preferably, each amino group is a tertiary amine. The symbols R and $R_1$ represent either hydrogen or a lower alkyl group. The term lower alkyl as used herein with regard to the basic amino function relates to groups having from 1 to 6 carbon atoms. Illustrative of such groups can be mentioned both straight or branched chain alkyl radicals such as: methyl, ethyl, n-propyl, isopropyl, n-butyl, sec-butyl, isoamyl, n-pentyl and n-hexyl. When R and $R_1$ each represent lower alkyl, a preferred subgenus is formed.

Each R and $R_1$ can also represent a cycloalkyl group having from 3 to 6 carbon atoms. Illustrative of such groups are the cyclopropyl, cyclobutyl, cyclopentyl and cyclohexyl radicals.

The symbols R and $R_1$ also represent an alkenyl group having from 3 to 6 carbon atoms. In addition to the unsaturation which must be present, this unsaturation must be in a position other than the 1-position of the alkenyl group in order to prevent hydrolysis from occurring. Illustrative of such groups are the allyl, 3-butenyl and the 4-hexenyl radicals.

R and $R_1$ may also be joined with the nitrogen atom to which they are attached to represent various saturated monocyclic, heterocyclic radicals. Typical of such heterocyclic groups are the 1-pyrrolidinyl, piperidino or morpholino radicals. Compounds containing these groups are readily prepared and typify saturated monocyclic, heterocyclic radicals which are generally useful in lieu of the dilower alkylamino groups present in the compounds of this invention.

The alkylene chain separating the basic amino function from the tricyclic ring consists of from 2 to 6 carbon atoms and can be either a straight or branched alkylene chain. The alkylene chain must separate the adjacent oxygen atom from the terminal amino nitrogen by at least 2 carbon atoms, i.e., the ester oxygen and amino nitrogen cannot share the same carbon atom of the alkylene group. Each of the alkylene groups can be the same or different, preferably, however, both alkylene groups are the same. Illustrative of such groups are ethylene, propylene, 1,3-propylene, butylene, 1,4-butylene, 2-methyl-1,4-butylene, pentamethylene, 3-methyl-1,5-pentylene and hexamethylene.

Illustrative of the base compounds of the present invention represented by general formula (I) above, there can be specifically mentioned: bis[3-(dibutylamino)propyl]5,6-dihydro-6-oxophenanthridine-3,8-dicarboxylate, bis(4-piperidinobutyl)5,6-dihydro-6-oxophenanthridine-3,8-dicarboxylate, bis[2-(diallylamino)ethyl]6-oxo-6H-dibenzo[b,d]pyran-3,8-dicarboxylate, bis[3-(N-cyclohexyl-N-methylamino)-propyl]6-oxo-6H-dibenzo[b,d]pyran-3,8-dicarboxylate, bis[3-(dimethylamino)propyl]-9-hydroxyphenanthrene-2,7-dicarboxylate and bis(5-morpholinopentyl)-9-hydroxyphenanthrene-2,7-dicarboxylate.

It must be also recognized that compounds of formula (I) in which a hydrogen is present in the 10-position of the phenanthrene nucleus as well as in the 5-position of the phenanthridine nucleus are capable of forming the corresponding enol tautomers. Thus, in both the 9-substituted phenanthrene and the 6(5H)-phenanthridone series, the compounds of the present invention may also be represented by the general formula (IA), which is tautomeric with the corresponding keto form as shown below.

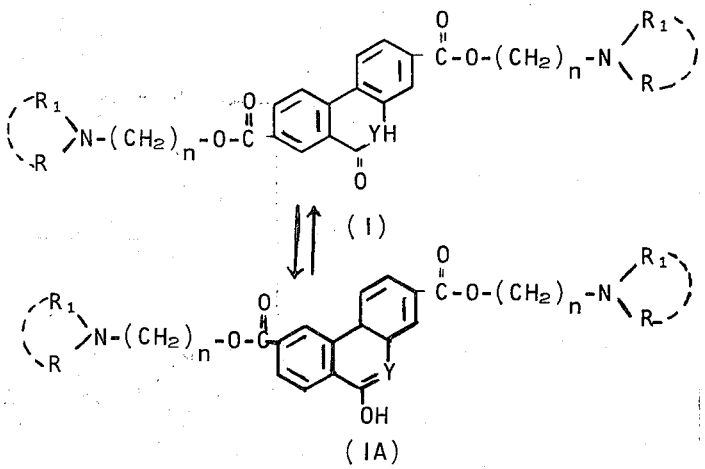

It is understood that Y is limited to nitrogen and CH. Where the oxygen atom is present, as in the 6H-dibenzo[b,d]pyran series, there is, of course, no enolizable hydrogen available and the compounds are present only in their keto form. It is further understood that the novel compounds of this invention are likely to be mixtures of tautomeric forms, the compositions of which are dependent upon such factors as the nature of the tricyclic nucleus, the various side chains present and the environment surrounding the molecule. In the case of the phenanthrene series, the enol or phenolic form predominates.

The enol form can be stabilized by a replacement of the enol hydrogen in this position with an alkyl group, such as $R_2$. Thus where the $R_2$ group is lower alkyl, the compounds of the present invention are represented by the general formula (II) above. In other words, the 6 and/or 9 lower alkyl ethers exist only in compounds of the phenanthridine and phenanthrene series, whereas the 6H-dibenzo[b,d]pyran series of compounds are incapable of enolizing and forming the corresponding 6-ether derivatives. Illustrative of the base compounds of the present invention represented by general formula (II) above, there can be specifically mentioned: bis[2-(diethylamino)ethyl]9-methoxyphenanthrene-2,7-dicarboxylate, bis[3-(dibutylamino)propyl]9-propoxyphenanthrene-2,7-dicarboxylate, bis(3-piperidinopropyl)9-ethoxyphenanthrene-2,7-dicarboxylate, bis(5-amino-2,2-dimethylpentyl)9-methoxyphenanthrene-2,7-dicarboxylate, bis[3-(dimethylamino)propyl]5,6-dihydro-6-propoxyphenanthridine-3,8-dicarboxylate, bis{2-[bis(3-butenyl)amino]ethyl}5,6-dihydro-6-ethoxyphenanthridine-3,8-dicarboxylate and bis(4-piperidinobutyl)5,6-dihydro-6-methoxyphenanthridine-3,8-dicarboxylate.

The expression "pharmaceutically acceptable acid addition salts" is intended to apply to any non-toxic organic or inorganic acid addition salts of the base compounds represented by formula (I). Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic and sulfonic acids such as methane sulfonic acid and 2-hydroxyethane sulfonic acid. Either the mono or the di-acid salts can be formed, and such salts can exist in either a hydrated or a substantially anhydrous form. In general, the acid addition salts of these compounds are crystalline materials which are soluble in water and various hydrophilic organic solvents and which in comparison to their free base forms, generally demonstrate higher melting points and an increased chemical stability.

In general the 9-(substituted)phenanthrone series of compounds and the 6(5H)-phenanthridone series of compounds are prepared via a ring expansion of the 2,7-bis basic esters of fluoren-9-one, disclosed in U.S. Pat. No. 3.662,062. More particularly the reaction of diazomethane with 2,7-bis-basic esters of fluoren-9-one results in the formation of 2,7-bis basic esters of 9-methoxyphenanthrene, whereas the reaction of 2,7-bis basic esters of fluoren-9-one with hydrazoic acid in the presence of a mineral acid results in the formation of 3,8-bis basic esters of 6(5H)-phenanthridinone.

Cyclic aliphatic ketones are known to ring expand with diazomethane to form larger cyclic aliphatic ketones. This reaction may also be conducted in some instances with aromatic ketones, producing a variety of homologous ring-enlarged ketones in addition to forming enols, enol ethers and ethylene oxides. Thus, for example, Schultz et al, J. Am. Chem. Soc. 62, 2902-4 (1940) reported the reaction of diazomethane with fluorenone to yield 5% of 9-phenanthrol, 30% of 9-methoxyphenanthrene, 1.5% of di-9-phenanthryl ether, an unknown substance and 30% of unchanged fluorenone. Substituents on the aromatic ring such as esters and ethers are known to change the ratio of the various products obtained as well as give rise to additional isomeric, homologous ketones and side products. Thus, the reaction of diazomethane with the 2,7-bis basic esters of fluoren-9-one could not have been predicted and is not without difficulty. The reaction is most frequently conducted by treatment of a methanolic solution of the carbonyl containing compound with an ethereal solution of diazomethane, either in the presence or absence of a catalyst. Alternatively, a solution of the carbonyl compound in methanol is treated with nitrosomethylurethane in the presence of a base. The diazomethane is prepared either ex situ or in situ. Generally, applicants prefer to generate the diazomethane ex situ and co-distill the diazomethane so produced with ether into a methanolic solution of the carbonyl containing compound. Suitable inert solvents which may be utilized include such solvents as dioxane, benzene, toluene, chloroform and methylene chloride with ether-methanol being the solvent combination of choice. Additionally, methanol has been known to have a high catalytic activity for diazomethane ring expansion reactions. Catalysts which may be usefully employed in this reaction include trace amounts of metal salts such as zinc chloride or lithium chloride. A minimum of 2 equivalents of diazomethane are generally employed, one equivalent providing for the ring expansion whereas the other equivalent provides for the formation of a methyl ether at the nine position in order to form the corresponding 9-methoxyphenanthrene (V). In addition to a variety of side products which are formed, some of the intermediate 2,7-bis basic esters of 9-phenanthrol (IV) also remain. These intermediates are readily separated from the reaction mixture in the form of their sodium salts. The 9-lower alkoxyphenanthrene derivatives (II), other than 9-methoxyphenanthrene derivatives are prepared, in turn, by the reaction of the 9-phenanthrols (IV) with other lower diazolalkanes.

Due to the complex and wide variety of side reactions possible, no more than 8 equivalents of diazomethane are useful in the preparation of the 2,7-bis-basic esters of 9-methoxyphenanthrene of the present invention. The reaction proceeds exothermally and is conducted at temperatures ranging from −50°C to ambient temperatures. For convenience a temperature of 0°C. is preferred with the reaction conducted for a period ranging anywhere from about 1 hour up to 7 days.

The 9-phenanthrol derivatives, which are also formed in the diazomethane ring expansion reaction are readily freed of nonacidic materials by extraction with chloroform from a strongly alkaline reaction mixture. The 9-phenanthrol derivatives which remain in the aqueous medium can be recovered by neutralization of the aqueous medium to a pH of about 9–10, and subsequently extracting the neutralized medium with chloroform.

Preparation of the bis basic esters of 6(5H)-phenanthridinone is achieved via a modification of the so-called Schmidt reaction. The 2,7-bis-basic esters of fluoren-9-one, when subjected to approximately equimolecular quantities of hydrazoic acid in the presence of a strong mineral acid such as sulfuric acid, undergo a ring expansion from the five-membered fluoren-9-one ring to the six-membered heterocyclic ring of 6(5H)-phenanthridinone. Hydrazoic acid is known to react with cyclic ketones to form ring-enlarged cyclic amides or lactams. The presence of two additional reactive carbonyl radicals in the form of esters which are subject to both attack by the reagent as well as to hydrolysis by the mineral acid employed, would appear to dictate against the use of the Schmidt reaction to prepare the bis-basic esters of 6(5H)-phenanthridinone. Nevertheless, under carefully controlled conditions hydrazoic acid will react with a fluoren-9-one to form a ring-enlarged cyclic lactam or 6(5H)-phenanthridinone. This reaction may be carried out using either a solution of hydrazoic acid in an appropriate organic solvent or by the addition of sodium azide directly to the reaction mixture. Due to the extremely poisonous nature of hydrazoic acid, the use of sodium azide is preferred, thus preparing the hydrazoic acid in situ. Because of the extreme rapidity with which hydrazoic acid is generated, the sodium azide is generally added to a stirred solution of the fluoren-9-one bis-basic esters in a suitable solvent. Suitable solvents include chloroform, benzene, dioxane and ethyl ether with trifluoroacetic acid having been found to be the solvent of choice. Inasmuch as the reaction is exothermic in nature, the stirred reaction mixture is also equipped with a cooling means. The temperature of the reaction mixture can be conveniently controlled by the rate at which hydrazoic acid is generated. The reaction is generally carried out at a temperature range of from −50° to 50°C. with a temperature range of from −10° to 10°C. being preferred. Any strong acid may be used as a catalyst for the reaction, however, applicants generally prefer to use a solution of concentrated sulfuric acid. The reaction takes place rapidly with the rate of reaction controlled essentially by the rate at which the hydrazoic acid is permitted to be generated. Generally, the reaction is conducted by the addition of sodium azide in small increments until no further evolution of nitrogen occurs. At this point the reaction is generally considered for all practical purposes to be complete. The bis basic esters of 6(5H)-phenanthridone so prepared are isolated and purified using standard procedures.

The 3,8-bis-basic esters of 6H-dibenzo[b,d]pyran-6-one are prepared by the oxidation, under modified Baeyer-Villiger conditions, of 9-oxo-fluorene-2,7-dicarboxylic acid (VII) to form the ring expanded cyclic lactone, 6H-dibenzo[b,d]pyran-6-one-3,8-dicarboxylic acid (VIII). Essentially the reaction results in a ring expansion of the 5-membered fluoren-9-one ring with the introduction of an oxygen atom to form the corresponding 6-membered ring-expanded lactone, or 6H-dibenzo[b,d]pyran-6-one. The reaction is exothermic in nature and the temperature of the reaction mixture may be conveniently controlled via the rate of addition of the oxidizing agent. Reaction temperatures vary from about −20° to 40°C., with a temperature of about 25°C. being preferred. Reaction times range anywhere from about 30 minutes to about one week at the lower temperatures. Large excesses of peroxide are to be avoided inasmuch as there is always the hazzard of peroxide oxidations occurring with explosive violence. If significant amounts of peroxides remain upon completion of the reaction, they can be decomposed using reducing agents such as sodium bisulfite or ferrous sulfate. Generally, a two or three fold excess of hydrogen peroxide is satisfactory in carrying out the ring expansion. The reaction is favored by polar solvents and proceeds in a variety of solvents such as sulfuric acid, acetic acid or acetic anhydride. The 6H-dibenzo[b,d]pyran-6-one-3,8-dicarboxylic acid (VIII) so prepared is subsequently esterified with an aminoalkyl halide using a variety of conventional procedures.

The compounds of the present invention are antiviral agents. Preferably they are administered to an animal host to prevent or inhibit viral infections. The term host refers to any viable biological material or intact animal including humans which is capable of inducing the formation of interferon and which serves as a support means for virus replication. The host can be of animal or mammalian origin. Illustratively such hosts include birds, mice, rats, guinea pigs, gerbils, ferrets, dogs, cats, cows, horses and humans. Other viable biological material such as used in the production of vaccines may also act as a host. Thus, tissue cultures prepared from organ tissues, such as mammalian kidney or lung tissue, as well as tissue cultures prepared from embryo tissue, such as obtained from amniotic cells or chick allantoic fluid, have been found to be useful hosts.

The treatment of virus infections for purposes of the present invention encompasses both the prevention and the inhibition of characteristic disease symptoms in a mammalian host susceptible to invasion by a pathogenic virus. Illustrative of mammalian virus infections which can be prevented or inhibited by the administration of the compounds of the present invention are infections caused by picornaviruses, such as encephalomyocarditis virus; myxoviruses, such as influenza $A_2$ (Jap/305) virus; arboviruses; such as Semliki forest virus; the herpes group of viruses, including herpes simplex; and the poxviruses, as for example vaccinia IHD. Thus, for example, the compounds of the present invention when administered orally or subcutaneously to mice in varying doses either shortly prior or subsequent to a fatal inoculation of a neurotropic virus such as encephalomyocarditis virus, having a $LD_{50}$ anywhere from 5 to 50, delay or prevent completely the onset of death. Salts of these compounds are generally administered in compositions containing a 0.15% aqueous hydroxyethylcellulose vehicle, whereas the free base compounds are generally administered in compositions containing a 10% aqueous surfactant vehicle in order to help solubilize the compound. In general, ten mice are used for each treated group with an additional 20 mice serving as a control group. At the time of administration the test virus is titrated in order to determine the potency or $LD_{50}$ for the particular virus pool used as a challenge. The control animals are given a placebo containing the identical volume of vehicle without, of course, the active ingredient. Because of the lethal nature of the test system employed, the antiviral nature of the test compound is dramatically illustrated by a side by side comparison of the survival time of treated animals with the untreated control group of animals.

Respiratory viruses, such as influenza $A_2$ (Jap/305) virus, which are also lethal to the test animals employed, are administered via intranasal instillation. Animals infected in this manner have the active ingredients administered in the same manner as the test virus, and again a side by side comparison is made of the survivors of the animals treated with the untreated control animals.

Inexplicably, a mouse fatally infected with encephalomyocarditis or influenza virus occasionally survives without further treatment. This may be the result of a prior, interferon-induced infection in the mouse, or perhaps due to some genetic factor or other natural defense mechanism not presently understood. For this reason the control group selected is of sufficient size as to statistically reduce to a negligible amount the influence of such a chance survivor upon the test results.

The vaccinia test virus is typical of the dermatotrophic type viruses which respond to treatment with compositions containing the compounds of the instant invention. The vaccinia virus generally produces a nonfatal infection in mice, producing characteristic tail lesions when the virus is subcutaneously administered to the tail of the mouse. The instant compounds are administered either orally or subcutaneously either prior to or subsequent to the vaccinia infection. Tail lesions are subjectively scored on the eighth day following infection against untreated animals which serve as a control group. The compounds of the present invention have been found to be effective in varying degrees against one or all of these test virus systems.

The mode of activity of the active ingredients of the present invention is not rigorously defined. Inter alia, the compounds of the present invention may induce the formation of interferon in a viable host. Interferon is a biological substance of unknown chemical structure, presumably proteinaceous in nature, which is produced by host cells in response to a viral infection. The interferon so produced acts to induce a virus inhibiting substance, which inhibits in some yet unknown manner the intracellular replication of the virus without appearing to have any inactivation effect per se upon the virus itself. A few of the viruses susceptible to interferon replication inhibition are described in Horsfall and Tamm, "Viral and Rickettsial Infections of Man" 4th Edition (1965), J.B. Lippincott Company, pp. 328-9.

As previously indicated, the compounds of the present invention may be prophylactically administered in order to prevent the spread of contagious viral diseases or they may be therapeutically administered to a host already infected intended for their curative effect. When administered prophylactically, it is preferred that the administration be made within 0 to 96 hours prior to the infection of the host animal with a pathogenic virus. When the compounds of the present invention are administered for their curative effect, it is preferred that they are administered within about 1 or 2 days following infection of the host in order to obtain the maximum therapeutic effect.

The dosage to be administered will be dependent upon such parameters as the particular virus for which either treatment or prophylaxis is desired, the species of animal involved, its age, health, weight, the extent of infection, concurrent treatment, if any, frequency of treatment and the nature of the effect desired. A daily dose of the active ingredients will generally range from about 0.1 mg to about 500 mg per kg of body weight. Illustratively dosage levels of the administered active ingredients for intravenous treatment range from about 0.1 mg to about 10 mg per kg of body weight; for intraperitoneal administration range from about 0.1 mg to about 50 mg per kg of body weight; for subcutaneous administration range from about 0.1 mg to about 250 mg per kg of body weight; for oral administration may be from about 0.1 mg to about 500 mg per kg of body weight; for intranasal instillation range from about 0.1 mg to about 10 mg per kg of body weight; and for aerosol inhalation therapy, the range is generally from about 0.1 mg to about 10 mg per kg of body weight.

The novel compounds described herein can also be administered in various different dosage unit forms, e.g., oral compositions such as tablets, capsules, dragees, lozenges, elixirs, emulsions, clear liquid solutions and suspensions; parenteral compositions such as intramuscular, intravenous or intradermal preparations; and topical compositions, such as lotions, creams or ointments. The amount of active ingredient contained in each dosage unit form will, of course, vary widely according to the particular dosage unit employed, the animal host being treated, and the nature of the treatment, i.e., whether prophylactic or therapeutic in nature. Thus, a particular dosage unit may contain from about 2.0 mg to over 3.0 g of active ingredient in addition to the pharmaceutical excipients contained therein.

The novel compounds described herein can be employed in conjunction or admixture with additional organic or inorganic pharmaceutical excipients. Suitable solid excipients include gelatin, lactose, starches, magnesium stearate and petrolatum. Suitable liquid excipients include water and alcohols such as ethanol, benzyl alcohol and the polyethylene alcohols either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5% to about 25% by weight, and preferably from about 1% to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil.

A suitable method of administration for the compounds of the present invention is orally either in a solid dose form such as a tablet or capsule, or in a liquid dose form such as an elixir, suspension, emulsion or syrup. Ordinarily the active ingredient comprises from about 0.5% to about 10% by weight of an oral liquid composition. In such compositions, the pharmaceutical carrier is generally aqueous in nature, as for example, aromatic water, a sugar-based syrup or a pharmaceutical mucilage. For insoluble compounds suspending agents may be added as well as agents to control viscosity, as for example, magnesium aluminum silicate or carboxymethylcellulose. Buffers, preservatives, emulsifying agents and other excipients can also be added.

For parenteral administration such as intramuscular intravenous or subcutaneous administration, the proportion of active ingredient ranges from about 0.05% to about 20% by weight, and preferably from about 0.1% to about 10% by weight of the liquid composition. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. The concentration of active ingredient contained in these various parenteral dosage unit forms varies over a broad range and comprises anywhere from about 0.05% to about 20% by weight of the total formulation, the remaining component or components comprising excipients previously mentioned.

The active ingredients of the present invention can also be admixed directly with animal feeds or incorporated into the drinking water of animals. For most purposes, an amount of active ingredient is used which provides from about 0.0001% to about 0.1% and preferably, from about 0.001% to about 0.02% by weight of the active ingredient based upon the total weight of feed intake. The active ingredients can be admixed in animal feed concentrates, suitable for use by farmers or livestock growers for incorporation in appropriate amounts with the final animal feeds. These concentrates ordinarily comprise from about 0.5% to about 95% by weight of the active ingredient compounded with a finely divided solid carrier or flour, such as wheat, corn, soybean or cottonseed flour. Depending upon the particular animal to be fed, nutrients and fillers may also be added such as ground cereal, charcoal, fuller's earth, oyster shells and finely divided attapulgite or bentonite.

The active ingredients of the present invention can be packaged in a suitable pressurized container together with an aqueous or volatile propellant for use as an aerosol. A suitable discharge valve is fitted to an opening in the container from which the active ingredients may be conveniently dispensed in the form of a spray, liquid, ointment or foam. Additional adjuvants such as co-solvents, wetting agents and bactericides may be employed as necessary. Normally, the propellant used is a liquified gaseous compound, preferably a mixture of low molecular weight fluorinated hydrocarbons. These haloalkanes are preferred because of their compatibility with the active ingredients of the present invention, and because they are non-irritating when applied to skin surfaces. Other useful propellants include ethylene oxide, carbon dioxide, propane and nitrogen gas.

The invention described herein is more particularly illustrated by means of the following specific examples:

EXAMPLE 1

Bis[3-(dibutylamino)propyl]9-oxo-fluorene-2,7-dicarboxylate dihydrochloride

A suspension of 30.5 g (0.10 mole) of 9-oxo-fluorene-2,7-dicarbonyl chloride in 1 liter of dry chloroform (ethanol free) is stirred and treated all at once with 37.5g (0.20 mole) of dry 3-dibutylamino-1-propanol causing a mildly exothermic reaction. The resulting mixture is stirred and refluxed for two hours, cooled to room temperature, filtered and the filtrate washed three times with 250 ml portions of a saturated sodium bicarbonate solution. The chloroform solution is washed with water and saturated sodium chloride solution, dried over anhydrous sodium sulfate and filtered. Most of the solvent is removed from the filtrate on the steam bath in vacuo and the remaining residue dissolved in butanone. This solution is made acid to Congo red with ethereal HCl causing the desired product to precipitate as a yellow crystalline solid. The bis [3-(dibutylamino)propyl]9-oxo-fluorene-2,7-dicarboxylate dihydrochloride so obtained is filtered, recrystallized from a butanone-methanol mixture and dried. The compound on standing in the atmosphere forms a monohydrate having a m.p. 178.5°–179.5°C., $\lambda_{max}^{H_2O}$ 276, and $E_{1cm}^{1\%}$ 1,370.

Following essentially the same procedure, the following bis basic esters of 9-oxo-fluorene-2,7-dicarboxylic acid are obtained: bis[2-(dimethylamino)ethyl]9-oxo-fluorene-2,7-dicarboxylate m.p. 254°–6°C. (dec.), $\lambda_{max}^{H_2O}$ 276, and $E_{1cm}^{1\%}$ 2,010; bis[2-(diisopropylamino)ethyl]9-oxo-fluorene-2,7-dicarboxylate dihydrochloride m.p. 245°–7°C. (dec.), $\lambda_{max}^{H_2O}$ 276, and $E_{1cm}^{1\%}$ 1,640; bis[2-(dihexylamino)ethyl]9-oxo-fluorene-2,7-dicarboxylate dihydrochloride m.p. 185°–6.5°C., $\lambda_{max}^{EtOH}$ 273.5, and $E_{1cm}^{1\%}$ 1,280; bis(2-morpholinoethyl)9-oxo-fluorene-2,7-dicarboxylate dihydrochloride m.p. 247°–8°C. (dec.), $\lambda_{max}^{H_2O}$ 276, and $E_{1cm}^{1\%}$ 1,627; bis[3-(diethylamino)propyl]9-oxo-fluorene-2,7-dicarboxylate dihydrochloride m.p. 251°–2°C. (dec.), $\lambda_{max}^{H_2O}$ 276, and $E_{1cm}^{1\%}$ 1,720; bis[4-(diethylamino)-1-methylbutyl]9-oxo-fluorene-2,7-dicarboxylate dihydrochloride m.p. 170°–90°C., $\lambda_{max}^{H_2O}$ 276, and $E_{1cm}^{1\%}$ 1,590; bis[2-(dibutylamino)ethyl]9-oxo-fluorene-2,7-dicarboxylate dihydrochloride m.p. 194°–5°C. (dec.), $\lambda_{max}^{H_2O}$ 276 and $E_{1cm}^{1\%}$ 1,480; bis[2-(N-methyl-N-cyclohexylamino)ethyl]9-oxo-fluorene-2,7-dicarboxylate dihydrochloride m.p. 252°C. (dec.), $\lambda_{max}^{H_2O}$ 276, and $E_{1cm}^{1\%}$ 1,600; bis[3-(dimethylamino)propyl]9-oxo-fluorene-2,7-dicarboxylate dihydrochloride m.p. 285°–6°C. (dec.), $\lambda_{max}^{H_2O}$ 276, and $E_{1cm}^{1\%}$ 1,890; bis[5-(diethylamino)pentyl]9-oxo-fluorene-2,7-dicarboxylate dihydrochloride m.p. 225°–6°C. (dec.), $\lambda_{max}^{H_2O}$ 276, and $E_{1cm}^{1\%}$ 1,590; bis[3-(diallylamino)propyl]9-oxo-fluorene-2,7-dicarboxylate dihydrochloride m.p. 234°–6°C. (dec.), $\lambda_{max}^{H_2O}$ 276, and $E_{1cm}^{1\%}$ 1,560; bis(3-piperidinopropyl)9-oxo-fluorene-2,7-dicarboxylate dihydrochloride m.p. 293°–5°C. (dec.), $\lambda_{max}^{H_2O}$ 276, and $E_{1cm}^{1\%}$ 1,690.

EXAMPLE II

Bis[3-(dibutylamino)propyl]5,6-dihydro-6-oxo-phenanthridine-3,8-dicarboxylate dihydrochloride To a solution of 20.4 g (0.03 mole) of bis[3-(dibutylamino)propyl]9-oxo-fluorene-2,7-dicarboxylate dihydrochloride and 13 ml of concentrated sulfuric acid contained in 150 ml of trifluoroacetic acid, which has been cooled to 0°C., is slowly added 2.6 g (0.04 mole) of sodium azide with stirring. Stirring is continued for 30 minutes whereupon most of the trifluoroacetic acid is removed in vacuo. Cracked ice is added and the residue is made alkaline with a 50% sodium hydroxide solution. The reaction mixture is extracted with methylene chloride, the extracts are combined, dried over magnesium sulfate, filtered and the filtrate treated with a slight excess of ethereal hydrogen chloride. The solution is concentrated to approximately 300 ml in vacuo, and approximately 500 ml of warm butanone is added. The mixture is permitted to cool slowly whereupon the desired bis[3-(dibutylamino)propyl]5,6-dihydro-6-oxophenanthridine-3,8-dicarboxylate crystallizes as the dihydrochloride salt. The product when recrystallized from a methylene chloride-ethyl acetate mixture has a m.p. 204.5°–6.5°C., and a N.E. of 349.4.

Following essentially the same procedure but substituting bis[3-(diethylamino)propyl]-9-oxo-fluorene-2,7-dicarboxylate dihydrochloride, bis(2-morpholinoethyl) 9-oxo-fluorene-2,7-dicarboxylate dihydrochloride, bis[3-(diallylamino)propyl]9-oxo-fluorene-2,7-dicarboxylate dihydrochloride and bis[5-(diethylamino)pentyl]9-oxo-fluorene-2,7-dicarboxylate dihydrochloride in lieu of the bis[3-(dibutylamino)propyl]9-oxo-fluorene-2,7-dicarboxylate dihydrochloride above, results in the preparation of bis[3-(diethylamino)propyl]5,6-dihydro-6-oxophenanthridine-3,8-dicarboxylate dihydrochloride, bis(2-morpholinoethyl)5,6-dihydro-6-oxophenanthridine-3,8-dicarboxylate dihydrochloride, bis[3-(diallylamino)propyl]5,6-dihydro-6-oxophenanthridine-3,8-dicarboxylate dihydrochloride and bis[5-(diethylamino)pentyl]5,6-dihydro-6-oxophenanthridine-3,8-dicarboxylate dihydrochloride.

EXAMPLE III

6-Oxo-6H-dibenzo[b,d]pyran-3,8-dicarboxylic acid

A suspension of 12.0 g (0.045 mole) of 9-oxo-fluorene-2,7-dicarboxylic acid in 100 ml of concentrated sulfuric acid is slowly reacted with 12.0 ml of a 30% hydrogen peroxide solution. The reaction is strongly exothermic and is controlled by cooling the stirred reaction mixture in a water bath. The cooled reaction mixture is poured onto 500 ml of an ice water mixture, filtered and washed with water. The residue is resuspended in water, stirred, filtered and washed with a total of about 350 ml of deionized water, to yield 11.2 g of 6-oxo-6H-dibenzo[b,d]pyran-3,8-dicarboxylic acid having a m.p. greater than 300°C.

EXAMPLE IV

Bis[3-(diethylamino)propyl]6-oxo-6H-dibenzo[b,d]-pyran-3,8-dicarboxylate dihydrochloride A mixture of 11.0 g (0.04 mole) of 6-oxo-6H-dibenzo[b,d]pyran-3,8-dicarboxylic acid, 18.0 g (0.12 mole) of γ-diethylaminopropyl chloride and 400 ml of isopropyl alcohol are stirred and heated to its reflux temperature. A catalytic amount of benzyltrimethylammonium chloride, 0.3 ml of a 60% aqueous solution, is added and the reaction mixture heated to reflux for an additional 24 hours. On cooling, the reaction mixture is filtered, and the residue washed with isopropyl alcohol. This product is dissolved in boiling ethanol, treated with charcoal, filtered and cooled to room temperature. After standing for 1 hour, the gelatinous precipitate which appears is filtered and the filtrate cooled to −20°C. The product which forms is filtered, washed with ethanol and again recrystallized from ethanol to yield the desired bis[3-(diethylamino)propyl]6-oxo-6H-dibenzo[b,d]pyran-3,8-dicarboxylate dihydrochloride as a tan-colored solid, soluble in water and having a m.p. of 250°–1°C. (dec.) (placed in m.p. bath previously heated at 240° C.), $\lambda_{max}$ 294, and $E_{1cm}^{1\%}$ 464.

EXAMPLE V

Bis[3-(dibutylamino)propyl]9-methoxyphenanthrene-2,7 dicarboxylate dihydrochloride A solution of 24.3 g (0.04 mole) of bis[3-(dibutylamino)propyl]9-oxo-fluorene-2,7-dicarboxylate in methanol is stirred and treated with approximately (0.12 mole) of diazomethane by co-distillation with ether into the reaction mixture at −10° to 30°C. After standing overnight at room temperature, the volatiles are removed from the reaction mixture on the steam bath under vacuum. The residue is dissolved in aqueous hydrochloric acid and extracted several times with ether. The aqueous solution is made strongly basic with aqueous sodium hydroxide, extracted with ether and the ether solution dried over anhydrous magnesium sulfate and filtered. The product is converted to its dihydrochloride salt using ethereal hydrogen chloride and purified by recrystallization. The aqueous solution remaining after extraction of bis[3-(dibutylamino)propyl]9-methoxyphenanthrene-2,7-dicarboxylate is saved for use in the following example.

EXAMPLE VI

Bis[3-(dibutylamino)propyl]9-hydroxyphenanthrene-2,7-dicarboxylate dihydrochloride The aqueous solution from the preceding example is adjusted to a pH of approximately 10 using a 10% hydrochloric acid solution. The aqueous solution is extracted several times with ether and the combined ether extracts are dried over anhydrous magnesium sulfate and filtered. The product contained in the filtrate is converted to the dihydrochloride salt using ethereal hydrogen chloride and further purified by recrystallization from ethanol.

The corresponding 9-ethoxy derivative is prepared by reacting a solution of bis[3-(dibutylamino)propyl]9-hydroxyphenanthrene-2,7-dicarboxylate in methanol with diazoethane by co-distillation with ether into the reaction mixture at −10° to 30°C. After standing overnight, the crude bis[3-(dibutylamino)propyl]9-ethoxyphenanthrene-2,7-dicarboxylate so obtained is converted to its dihydrochloride salt by the addition of ethereal hydrogen chloride.

EXAMPLE VII

The following Example is illustrative of the antiviral activity for the compounds of the present invention.

Thirty mice each weighing approximately 12 to 15 gms are divided into two groups, a control group containing 20 animals and a test group of 10 animals. All of the animals are challenged with a fatal dose ($13LD_{50}$) of encephalomyocarditis virus. The test group of animals are tested both prophylactically and therapeutically using a parenteral composition containing bis[3-(diethylamino)propyl]6-oxo-6H-benzo[b,d]pyran-3,8-dicarboxylate dihydrochloride as the active ingredient dissolved in an aqueous solution of 0.15% hydroxyethylcellulose. The composition contains the active ingredient in an amount such that each dosage contains 0.25 ml which is equivalent to a dose level of 50 mg per kg. The control group receives a subcutaneous placebo containing the same volume of vehicle without, of course, the active ingredient. Observations over a ten day period show a termination of all the control animals within a period of from 4 to 5 days, with the treated group of animals surviving for a statistically longer period of time.

EXAMPLE VIII

Preparation of a tablet formulation

An illustrative preparation of 10,000 tablets, each containing 100 mg of bis[3-(diethylamino)propyl]6-oxo-6H-dibenzo[b,d]pyran-3,8-dicarboxylate dihydrochloride is prepared as follows:

| | | Gm. |
|---|---|---|
| (a) | Bis[3-(diethylamino)propyl] 6-oxo-6H-dibenzo[b,d]pyran-3,8-dicarboxylate dihydrochloride | 1000 |
| (b) | Lactose | 1000 |
| (c) | Starch paste (10% w/v starch in water) | 100 |
| (d) | Starch | 32.5 |
| (e) | Calcium stearate | 6.5 |

The active ingredient is uniformly mixed with the lactose and granulated by the addition of the starch paste. The granules which form are dried at 120°F. for 20 hours and forced through a No. 16 screen. The granules are lubricated by the addition of the starch and calcium stearate and compressed into tablets. Each tablet so prepared contains 100 mg of the active ingredient.

EXAMPLE IX

Preparation of a capsule formulation

An illustrative composition for the preparation of 1000 two-piece hard gelatin capsules, each capsule containing 100 mg of bis(4-piper idinobutyl)5,6-dihydro-6-methoxyphenanthridine-3,8-dicarboxylate dihydrochloride is prepared as follows:

| | | Gm. |
|---|---|---|
| (a) | Bis(4-piperidinobutyl)5,6-dihydro-6-methoxyphenanthridine-3,8-dicarboxylate dihydrochloride | 100 |
| (b) | Corn starch | 150 |
| (c) | Magnesium stearate | 25 |
| (d) | 1000 hard gelatin capsules | |

The finely powdered ingredients are mixed until uniformly dispersed and then filled into hard shelled gelatin capsules of the appropriate size.

In a similar fashion, soft gelatin capsules may be prepared in which the above composition can be granulated, slugged or directly compressed in a rotary die or plate mold in which the soft gelatin capsule is formed. Alternatively, the above excipients may be omitted and the active ingredients dispensed as a powder directly into the soft gelatin capsule.

EXAMPLE X

Preparation of an oral syrup formulation

A 2% weight per volume syrup of bis[2-(diethylamino) ethyl]9-methoxyphenanthrene-2,7-dicarboxylate dihydrochloride is prepared in accordance with the usual pharmaceutical techniques which has the following formula:

| | | Gms. |
|---|---|---|
| (a) | Finely divided bis[2-(diethylamino)ethyl]9-methoxyphenanthrene-2,7-dicarboxylate dihydrochloride | 2.0 |
| (b) | Sucrose | 33.3 |
| (c) | Chloroform | 0.25 |
| (d) | Sodium benzoate | 0.4 |
| (e) | Methyl p-hydroxybenzoate | 0.02 |
| (f) | Vanillin | 0.04 |
| (g) | Glycerol | 1.5 |
| (h) | Purified water to 100.0 ml | |

EXAMPLE XI

Preparation of an ointment formulation

One thousand grams of an ointment for topical application containing 1.0% of bis[2-(dimethylamino)ethyl]6-oxo-6H-dibenzo[b,d]pyran-3,8-dicarboxylate dihydrochloride is prepared from the following ingredients:

| | | Gm. |
|---|---|---|
| (a) | Bis[2-(dimethylamino)ethyl] 6-oxo-6H-dibenzo[b,d]pyran-3,8-dicarboxylate dihydrochloride | 10 |
| (b) | Light liquid petrolatum | 250 |
| (c) | Wool fat | 200 |
| (d) | White petrolatum q.s. ad 1000 | |

The wool fat, white petrolatum and 200 gms of the light liquid petrolatum are liquified and held at 110°F. The active ingredient is mixed with the remaining liquid petrolatum and passed through a colloid mill. After passing through the mil, the mixture is stirred into the melt, and the melt is permitted to cool with continued stirring until congealed.

EXAMPLE XII

Preparation of a parenteral formulation

An illustrative composition for an emulsion which is parenterally injectable is as follows:

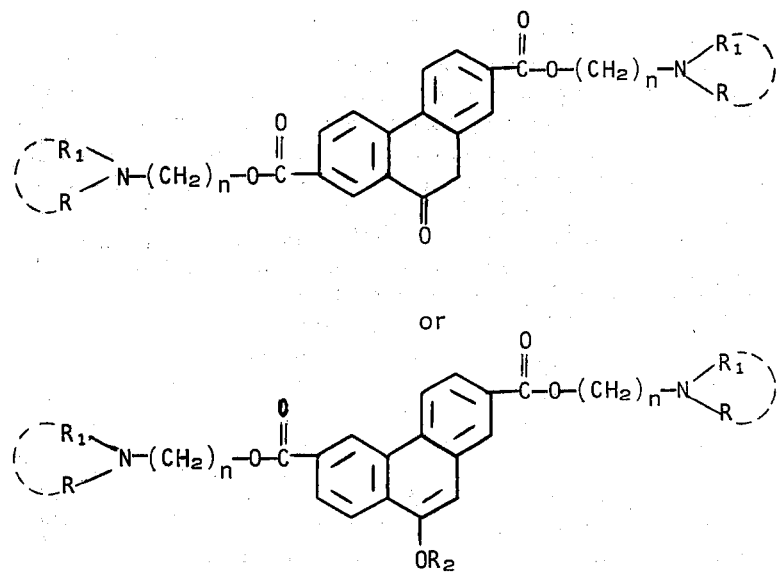

| Each ml Contains | Ingredients | Amount |
|---|---|---|
| 50 mg | Bis[3-(dibutylamino)propyl] 5,6-dihydro-6-oxophenanthridine-3,8-dicarboxylate dihydrochloride | 1.000 g |
| 100 mg | Polyoxyethylene sorbitan monooleate | 2.000 g |
| 0.0064 | Sodium chloride | 0.128 g |
| | Water for injection, q.s. | 20.000 ml |

The parenteral composition is prepared by dissolving 0.64 g of sodium chloride in 100 ml of water suitable for injection. The polyoxyethylene sorbitan monooleate is mixed with the active ingredient, and an amount of the previously prepared aqueous sodium chloride solution is added which is sufficient to bring the total volume to 20 ml. The resulting solution is shaken and autoclaved for 20 minutes at 110°C. at 15 p.s.i.g. steam pressure. The composition can be dispensed in single ampule for use in multiple dosages or it can be dispensed as 10 or 20 individual ampules for use as a single dosage unit.

We claim:

1. A derivative of 9-phenanthrone having the formula:

wherein $n$ is an integer of from 2 to 6; R and $R_1$ are each selected from the group consisting of hydrogen, lower alkyl having from 1 to 6 carbon atoms, cycloalkyl having from 3 to 6 carbon atoms, alkenyl having from 3 to 6 carbon atoms in which the unsaturation is in a position other than in the 1-position of the alkenyl group, and when R and $R_1$ are taken together with the nitrogen atom to which they are attached represent the pyrrolidinyl, piperidino or morpholino radical; $R_2$ is selected from the group consisting of hydrogen or lower alkyl having from 1 to 4 carbon atoms; and the pharmaceutically acceptable acid addition salts thereof.

2. A compound according to claim 1 wherein R and $R_1$ are each lower alkyl.

3. A compound according to claim 1 which is bis[3-(dibutylamino)propyl]9-methoxyphenanthrene-2,7-dicarboxylate and its pharmaceutically acceptable acid addition salts.

4. A compound according to claim 1 which is bis[3-(dibutylamino)propyl]9-hydroxyphenanthrene-2,7-dicarboxylate and its pharmaceutically acceptable acid addition salts.

* * * * *